US008998468B2

(12) United States Patent
Jaffe et al.

(10) Patent No.: US 8,998,468 B2
(45) Date of Patent: Apr. 7, 2015

(54) SOLID STATE LIGHT SOURCE WITH HYBRID OPTICAL AND ELECTRICAL INTENSITY CONTROL

(71) Applicant: Lumencor, Inc., Beaverton, OR (US)

(72) Inventors: Claudia B. Jaffe, Portland, OR (US); Steven M. Jaffe, Portland, OR (US)

(73) Assignee: Lumencor, Inc., Beaverton, OR (US)

( * ) Notice: Subject to any disclaimer, the term of this patent is extended or adjusted under 35 U.S.C. 154(b) by 162 days.

(21) Appl. No.: 13/788,022

(22) Filed: Mar. 7, 2013

(65) Prior Publication Data

US 2013/0242595 A1    Sep. 19, 2013

Related U.S. Application Data

(60) Provisional application No. 61/611,910, filed on Mar. 16, 2012.

(51) Int. Cl.
| | |
|---|---|
| *F21V 7/04* | (2006.01) |
| *F21V 11/00* | (2006.01) |
| *A61B 1/06* | (2006.01) |
| *G02B 21/16* | (2006.01) |
| *G02B 27/14* | (2006.01) |
| *F21V 8/00* | (2006.01) |

(52) U.S. Cl.
CPC ............... *F21V 11/00* (2013.01); *A61B 1/0638* (2013.01); *G02B 21/16* (2013.01); *G02B 27/141* (2013.01); *A61B 1/0669* (2013.01); *A61B 1/0684* (2013.01); *G02B 6/0003* (2013.01); *G02B 6/0006* (2013.01)

(58) Field of Classification Search
CPC ....................................................... F21V 11/00
USPC ................ 362/552, 231, 249.02, 249.05
See application file for complete search history.

(56) References Cited

U.S. PATENT DOCUMENTS

| | | | |
|---|---|---|---|
| 7,709,811 B2 | 5/2010 | Conner | |
| 7,846,391 B2 | 12/2010 | Jaffe et al. | |
| 7,898,665 B2 | 3/2011 | Brukilacchio et al. | |
| 8,098,375 B2 | 1/2012 | Brukilacchio | |
| 8,242,462 B2 | 8/2012 | Jaffe et al. | |
| 8,258,487 B1 | 9/2012 | Jaffe et al. | |
| 8,263,949 B2 | 9/2012 | Jaffe et al. | |
| 8,279,442 B2 | 10/2012 | Brukilacchio et al. | |

(Continued)

OTHER PUBLICATIONS

International Search Report dated Jun. 3, 2013 for PCT/US2013/029931, 11 pages.

*Primary Examiner* — Vip Patel
(74) *Attorney, Agent, or Firm* — Meyer IP Law Group

(57) ABSTRACT

A solid state illumination system is provided as a replacement for conventional arc light, metal halide and Xenon light sources for applications in microscopy, fluorescence microscopy, and endoscopy. The illumination system includes hybrid optical and electrical control of output intensity in which the light output of one or more of the light sources is attenuated optically such that it is not necessary to reduce the electrical drive power/current of the LEDs at a level where the spectral power distribution is variable. One or more fixed, selectable, or variable neutral density filters is interposed in the output beam of one or more sources to achieve optical attenuation of the light output. The hybrid optical and electrical control of output intensity allows greater dynamic range of intensity to be achieved than could be achieved with electrical control of the LEDs alone while maintaining the desired spectral power distribution.

25 Claims, 8 Drawing Sheets

(56) References Cited

U.S. PATENT DOCUMENTS

| | | |
|---|---|---|
| 8,309,940 B2 | 11/2012 | Jaffe et al. |
| 8,389,957 B2 | 3/2013 | Jaffe et al. |
| 8,466,436 B2 | 6/2013 | Jaffe et al. |
| 8,493,564 B2 | 7/2013 | Brukilacchio et al. |
| 8,525,999 B2 | 9/2013 | Brukilacchio |
| 8,625,097 B2 | 1/2014 | Brukilacchio et al. |
| 8,629,982 B2 | 1/2014 | Brukilacchio |
| 8,673,218 B2 | 3/2014 | Jaffe et al. |
| 8,698,101 B2 | 4/2014 | Jaffe et al. |
| 8,728,399 B2 | 5/2014 | Jaffe et al. |
| 2003/0007087 A1 | 1/2003 | Hakamata et al. |
| 2007/0009210 A1 | 1/2007 | Hulse |
| 2011/0044858 A1 | 2/2011 | Jaffe et al. |
| 2013/0188331 A1 | 7/2013 | Jaffe et al. |
| 2013/0188383 A1 | 7/2013 | Jaffe et al. |
| 2013/0188384 A1 | 7/2013 | Jaffe et al. |
| 2013/0188388 A1 | 7/2013 | Jaffe et al. |
| 2013/0234047 A1 | 9/2013 | Jaffe et al. |
| 2013/0335992 A1 | 12/2013 | Jaffe et al. |
| 2014/0098560 A1 | 4/2014 | Brukilacchio |
| 2014/0119006 A1 | 5/2014 | Brukilacchio et al. |
| 2014/0192405 A1 | 7/2014 | Jaffe et al. |

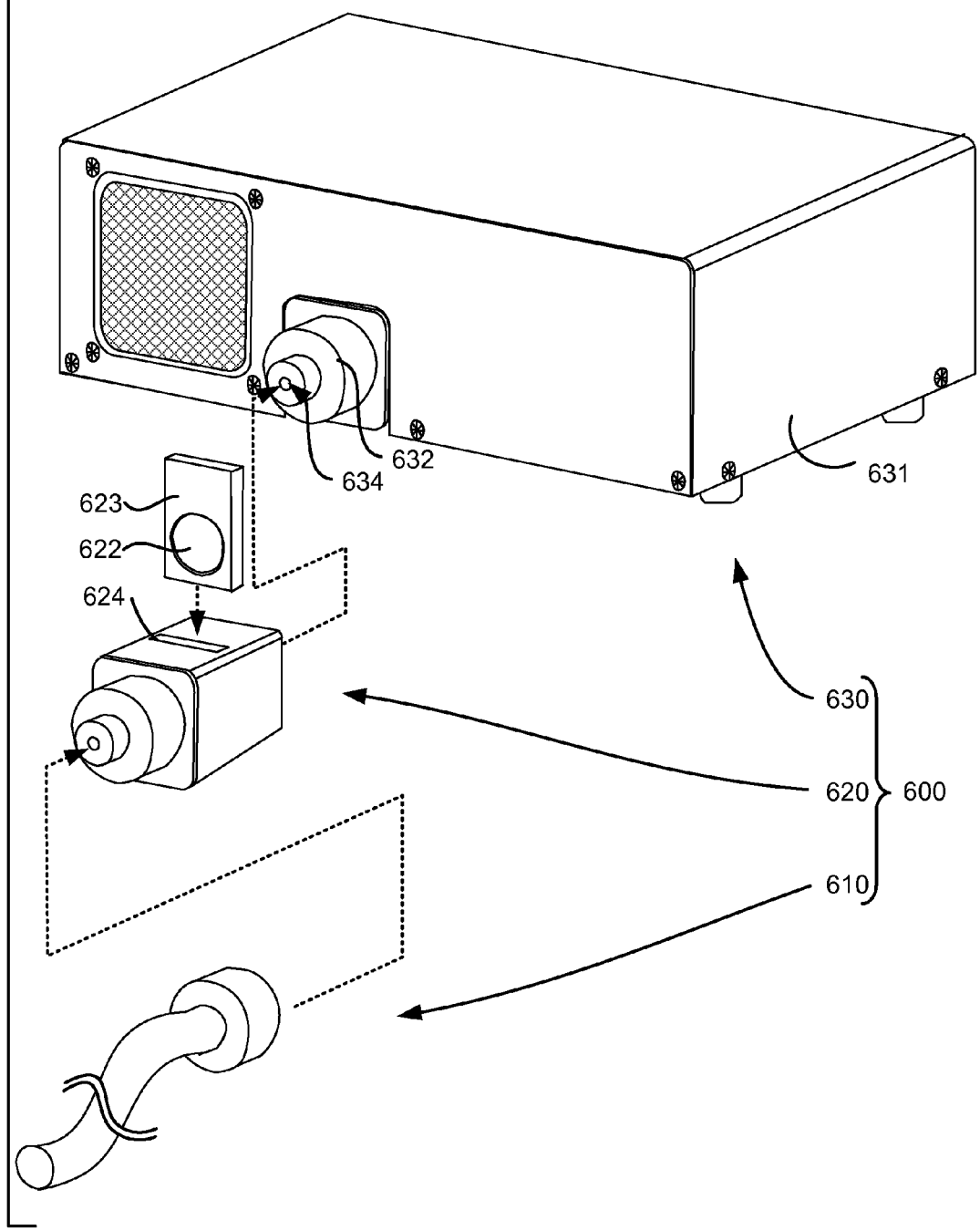

SOLID STATE LIGHT SOURCE WITH HYBRID OPTICAL AND ELECTRICAL INTENSITY CONTROL

CLAIM OF PRIORITY

This present application claims the benefit of priority to U.S. Provisional Patent Application No. 61/611,910, entitled "SOLID STATE LIGHT SOURCE WITH HYBRID OPTICAL AND ELECTRICAL INTENSITY CONTROL", filed on Mar. 16, 2012, all of which applications are incorporated herein by reference in their entirety.

RELATED APPLICATIONS

The present application is related to the following patent applications which are incorporated herein by reference:

U.S. Provisional Application No. 61/644,921, filed May 9, 2012, entitled "Solid State Continuous White Light Source";

U.S. Provisional Application entitled "Solid State Continuous White Light Source" Ser. No. 61/589,086 filed Jan. 20, 2012;

U.S. Patent Application entitled "Lighting Design of High Quality Biomedical Devices," Publication No. 2010/0187440 filed Jan. 21, 2010;

U.S. Patent Application entitled "Bioanalytical Instrumentation Using A Light Source Subsystem," Publication No. 2007/0281322 filed May 21, 2007;

U.S. Patent Application entitled "Light Emitting Diode Illumination System," Publication No. 2009/0008573 filed Jul. 2, 2008;

U.S. Patent Application entitled "Light Emitting Diode Illumination System," Publication No. 2009/0040523 filed Aug. 5, 2008; and U.S. Patent Application entitled "Light Emitting Diode Illumination System," Publication No. 2011/0116261 filed Jan. 24, 2011.

FIELD OF THE INVENTION

The present invention relates to lighting systems for microscopy, fluorescence microscopy, and endoscopy. In particular the present invention relates to a solid state light source for microscopy and fluorescence microscopy.

BACKGROUND OF THE INVENTION

Among the trends redefining 21st century biomedical diagnostics and therapeutics is the design of low-cost portable analyzers. Because light is a powerful tool in many of today's most widely used life science instruments, high intensity, low cost light engines are essential to the design and proliferation of the newest bio-analytical instruments, medical devices and miniaturized analyzers. The development of new light technology represents a critical technical hurdle in the realization of point-of-care analysis.

Lighting for life sciences is a broad and general category. Not only are the source specifications varied but so too are the equally important optical delivery requirements. Spectral and spatial lighting requirements for sensing on the head of an optical probe or within a single cell in a flowing stream differ in output power by orders of magnitude from the requirements of a multi-analyte detection scheme on an analysis chip or within the wells of a micro-titer plate. The number of colors, spectral purity, spectral and power stability, durability and switching requirements are each unique. Illuminating hundreds of thousands of spots for quantitative fluorescence within a micro-array may be best served by projection optics while microscopes set demanding specifications for light delivery to overfill the back aperture of the microscope objective within optical trains specific to each scope body and objective design.

Historically arc lamps are noted to be flexible sources in that they provide white light. The output is managed, with numerous optical elements, to select for the wavelengths of interest and for typical fluorescence based instruments, to discriminate against the emission bands. However their notorious instability and lack of durability in addition to their significant heat management requirements make them less than ideal for portable analyzers. Moreover, large power demands to drive them present a barrier to battery operation within a compact design.

Lasers require a trained user and significant safety precautions. While solid state red outputs are cost effective, the shorter wavelength outputs are typically costly, require significant maintenance and ancillary components. Color balance and drift for multi-line outputs is a serious complication to quantitative analyses based on lasers. Moreover, the bulk of fluorescence applications do not need coherent light, are complicated by speckle patterns and do not require such narrow band outputs. Overcoming each of these traits requires light management and adds cost to the implementation of lasers for most bio-analytical tools.

Finally LEDs have matured significantly within the last decades. LEDs are now available in a relatively wide range of wavelengths. However their output is significantly broad so as to require filtering. Additionally, output in the visible spectrum is profoundly reduced in the green, 500-600 not. The LED also presents trade-offs with respect to emission wavelength dependent intensity, broad emission spectrum (spectral half width on the order of 30 nm or more), poor spectral stability, and the wide angular range of emission. In addition, the process used to manufacture LED's cannot tightly control their spectral stability; anyone wishing to use LED's in applications requiring a good spectral stability must work directly with a supplier to essentially hand-pick the LED's for the particular application. Finally, LED's generate light over a wide angular range (50% of light intensity emitted at 70°). While optics can narrow the emission band and focus the light output, the resulting loss in power and increase in thermal output further limit the feasibility of LED light engines.

Most importantly, these light technologies cannot be fundamentally improved for bioanalytical applications. The associated light engine market simply does not justify the large investment necessary to overcome fundamental performance limitations. As a result, analytical instrument performance and price is constrained by the light source with no clear solution in sight. Moreover the numerous manufacturers of lamps and lasers provide only a source, not an integrated light engine. Companies such as ILC Technology, Lumileds, Spectra-Physics, Sylvania and CoolLED require some sort of mechanics and or electro-optics such as acousto-optic tunable filters (AOTFs), excitation filters (with a wheel or cube holder), shutters and controllers.

SUMMARY OF THE INVENTION

The present invention provides an inexpensive lighting solution, uniquely well suited to the production of safe, effective and commercially viable life science tools and biomedical devices attained using the solid-state light engine as described. In an embodiment of the invention, this light engine can provide powerful, pure, stable, inexpensive light across the visible spectrum and at a large user controllable range of intensities. Light engines are designed to directly replace the entire configuration of light management components with a single, simple unit. Power, spectral breadth and purity, stability and reliability data will demonstrate the advantages of these light engines for today's bioanalytical needs. Performance and cost analyses can be compared to traditional optical subsystems based on lamps, lasers and LEDs with respect to their suitability as sources for biomedical applications, implementation for development/evaluation of novel measurement tools and overall superior reliability. Using such sources the demand for portable, hand-held analyzers and disposable devices with highly integrated light sources can be fulfilled.

Embodiments of the present invention are directed to a solid state light subsystem suitable for use as a replacement for conventional arc light, Metal Halide and Xenon white-light subsystems for applications in microscopy, fluorescence microscopy, and endoscopy. Embodiments of the invention utilize hybrid optical and electrical intensity control to allow for a wide range of user selectable output intensity without significant variation in the spectral power distribution of the output light. In embodiments the hybrid optical and electrical intensity control allows for greater dynamic range of intensity without significant variation in the spectral power distribution than would be achievable with purely electronic control of LED output. In particular embodiments, the solid state light subsystem generates white light which is continuous in the visible spectrum from 380 nm to 650 nm. In other embodiments the solid state light subsystem generates selectable colors (wavelengths) of light within the visible spectrum from 380 nm to 650 nm In particular embodiments the solid state light subsystem incorporates one or more light pipe engines.

One embodiment of the present invention is directed to an illumination system, comprising: a plurality of LED light sources, wherein each of the plurality of LED light sources emits output light of a different spectral power distribution than each other of the first plurality of LED light sources; an LED control circuit which controls the electrical power provided to the first plurality of LED light sources such that intensity of light emitted by each of the plurality of LED light sources can be varied over a range; associated optics, wherein the associated optics combine the output light of different colors emitted by the first plurality of LED light sources into a combined output light having a combined spectral power distribution; and one or more optical attenuator interposed between one or more of the plurality of light sources and the associated optics such that output light of one or more of the plurality of light sources is attenuated prior to combination by the associated optics; whereby the combined output light has an intensity which can be varied over a desired range without substantially changed the combined spectral power distribution of the combined output light.

In particular embodiments the present invention is directed to a to a solid state white-light subsystem which emits white light having a spectral power equal to or greater than the spectral power of a 120 W metal halide lamp or 150 W Xenon lamp across substantially the entire visible spectrum from 380 nm to 650 nm. In particular embodiments the spectral power is greater than 1 mW/nm over the substantially the entire visible spectrum from 380 nm to 650 nm and greater than 3 mW/nm over the range from 500-600 nm. Embodiments of the invention utilize hybrid optical and electrical intensity control such that the output intensity can be linearly controlled without substantially altering the relative spectral power distribution of the light.

In an embodiment of the present invention, an illumination system can emit high quality white light. In an embodiment of the present invention, the illumination system can be pulsed on and off as desired to reduce heat generation. In an embodiment of the present invention, an illumination and collection system can be pulsed on and off to allow time-based fluorescence detection.

Other objects and advantages of the present invention will become apparent to those skilled in the art from the following description of the various embodiments, when read in light of the accompanying drawings.

BRIEF DESCRIPTION OF THE FIGURES

Various embodiments of the present invention can be described in detail based on the following figures, wherein:

FIG. 6A shows a white light illumination system according to an embodiment of the present invention;

DETAILED DESCRIPTION OF THE INVENTION

Figure 1:
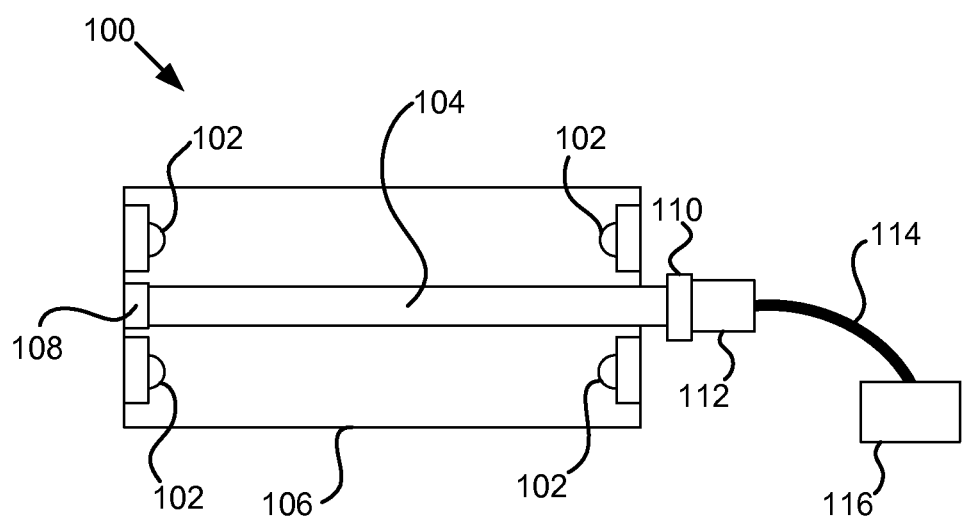
FIG. 1 shows a schematic of a light engine subsystem consisting of a lamp module and delivery optics.

While lighting manufacturers cannot provide all things to all applications, it is precisely this breadth of demand for which a light engine can be designed. To that end, products are not simple sources, but rather light engines: sources and all the ancillary components required to provide pure, powerful, light to the sample or as close to it as mechanically possible. Such designs have resulted in products that embody a flexible, hybrid solution to meet the needs of the broad array of applications for biotech. A qualitative comparison of light engine performance as a function of source technology is summarized in Table 1.

TABLE I

A qualitative comparison of light engine performance as function of the source technology employed

| Source Technology | Useable Light | Uniformity | Temporal Response | Heat Generation | Durability | Cost |
|---|---|---|---|---|---|---|
| Arc Lamp | med | poor | none | high | low | high |
| Laser | high | poor | none | low | low | very high |
| LED | low | poor | fast | low | high | medium |
| Tungsten | low | poor | none | medium | low | medium |
| Light Pipe | high | high | fast | low | high | low |

Light Pipe Engines

While no one lighting solution can best satisfy all instrument architectures, a light pipe engine combines the best of solid state technologies to meet or outperform the traditional technologies listed in Table I on the basis of all figures of merit for all individual wavelengths. Key to this performance is the light pipe architecture. Single outputs, such as red from a diode laser, may be competitive. However, no family of outputs can by assembled that bests the light pipe disclosed herein. In an embodiment of the invention, a light pipe engine can emit narrowband light exceeding 500 mW/color with intensifies up to 10 W/cm$^2$ depending on the application. In an embodiment of the invention, bandwidths as narrow as 10 nm are achievable. While such output power and overall emission intensity is impressive, the most significant figure of merit for quantifying the value of any lighting subsystem for bio-analytics is the intensity of high quality illumination provided to the sample. This is a factor dictated by the instrument design and sample volume and clearly very application specific.

In the case of medical devices and portable diagnostics the present light pipe invention offers a smart alternative for light generation. The light pipe engine is an optical subsystem; it consists of lamp modules for each discrete output based on solid state technologies tailored to best satisfy that output requirement complete with collection and delivery optics. The capabilities of the light pipe engine are highlighted in Table 2. The high performance illumination provided by the light pipe engine is embodied in a single compact unit designed to replace the entire ensemble of lighting components. The sources, excitation filters, multicolor switching capabilities and fast pulsing are contained within one box such that no external optics or mechanics are required.

TABLE II

Light pipe engine metrics of light pipe engines designed to meet the needs for portable fluorescence assays and biomedical devices.

Key Metrics:

| | |
|---|---|
| Spectral Output | Up to eight colors spanning UV-Vis-NIR |
| | >_ 100 mW/spectral band |
| | 1-10 W/cm |
| Peak Wavelength | Optimal for different floors, adjustable bandwidths |
| Power Stability | >99% over 24 hours |
| Spectral Width | 10 to 50 nm |
| Spectral Drift | <1% in 24 hours |
| Color Dependence | None |
| Lifetime | >5000 hrs |
| Footprint | amenable to portability |
| Maintenance | None, no replacement components for the light engines lifetime |

In various embodiments of the present invention, a lamp emits wavelengths of light, which excite fluorescence from photosensitive targets in the sample of interest. In various embodiments of the present invention, a lamp can be in the form of a tube, rod, or fiber of varying or constant diameter. In various embodiments of the present invention, a constituent light pipe can be made of glass, plastic, single or multiple inorganic crystal(s), or a confined liquid. In various embodiments of the present invention, a pipe either contains or is coated with a layer or layers containing, a narrow band luminescent material such as organic or inorganic compounds involving rare earths, transition metals or donor-acceptor pairs. In various embodiments of the present invention, a lamp emits confined luminescence when excited by IR, UV, or visible light from an LED, Laser, fluorescent tube, arc lamp, incandescent lamp or other light source. In an embodiment of the present invention, a lamp operates through the process of spontaneous emission, which results in a much larger selection of available wavelengths than is available for efficient stimulated emission (laser action). A number of lamps each emitting one or more color of light can have their constituent light pipes coupled in parallel or in series acting to produce multiple colors simultaneously or in sequence. Lamps can be illuminated continuously d or can be pulsed on and off rapidly to enable time-based detection methods. A lamp can be switched off between measurements, to eliminate the heat output. This can be contrasted with alternatives such as arc lamps or lasers that are unstable unless they are operated continuously.

Shown in FIG. 1, is the light pipe engine 100 of an embodiment of the invention. An individual lamp module driven by light pipe technology consists of an excitation source 102, typically one or more LEDs, and a light pipe 104. In an embodiment, the excitation source 102 and light pipe 104 can be housed in a cylindrical waveguide 106. The excitation source 102 drives luminescence in the light pipe 104, which is composed of a glass or polymer fiber. In an embodiment, light pipe 104 includes a mirror 108. Glass fibers are either doped with a rare earth metal or activated with a transition metal. Polymer fibers are doped with a dye. The fibers have fast response and decay times and can achieve a high efficiency through the design of delivery optics. The design and selection of the fiber determines the peak wavelength of the output illumination; options exist to span the UV-Vis-NIR spectrum. The bandwidth of the luminescence is narrow and can be further defined with the use of band pass filters 110 integrated into the delivery optics. In an embodiment, the delivery optics may include a band pass filter 110 connected to a coupler 112, which can be attached to an optical delivery pipe 114 which leads to an instrument (e.g., a microtiter plate) 116. Output intensity is determined through the design of the pipe's excitation source.

The light pipe geometry provides a unique opportunity to shape and direct the angular and spatial range of outputs. Combined with a high output power, the delivery optics can be readily tailored to couple the light with various instruments and analyzers. Sensors, optical probes, microscope objectives or through liquid light guides, two-dimensional oligomer and micro fluidic chips, and micro titer plates are all illumination fields that light pipe engines can readily support. Moreover, high output power enables illumination of large areas within a chip, micro array or micro titer plate and, as a result, support high-speed throughput in instruments where to date only scanning modes of operation could be envisioned.

The preferred mode of light pipe excitation is the application of one or more LED's. This approach takes advantages of the benefits of LED illumination: low cost, durability, and, at an appropriate excitation wavelength, high output power to drive the light pipe. In so doing the LED's shortcomings are managed. The lack of spectral stability and the high angular output characteristic of LED's do not impact the luminescence of the light pipe. Instead, the innovation of the light pipe enables circumvention of the principle of etendue conservation. All light sources must conform to this dictate, which requires the spread of light from a source never exceed the product of the area and the solid angle. Etendue cannot decrease in any given optical system.

The ability to modulate solid-state source outputs provides a unique opportunity for multiplexed fluorescent assays. Current light engine designs employ solid state materials with fast luminescence (approximately 10 ns.) The light pipe and LED have similar modulation capabilities thus multiple light pipes tuned to different output wavelengths can be employed to selectively detect multiple fluorescent tags within a given analysis. In addition, pulse modulation and phase modulation techniques enable fluorescence lifetime detection and afford improved signal to noise ratios. Each of the solid state units is truly off when it is off so low background signals and high contrast ratios are possible.

Table III shows an embodiment of the present light pipe engine invention's product and performance features. As improvements are made to LED's and the cost of semiconductor lasers continue to decline, the tool chest of options available to light pipe engines will continue to evolve. The desired light engine can ultimately be powered by a combination of light pipe, LED's and lasers. The knowledge and competency to integrate any of these lighting technologies into the delivery optics supports the requirements of each specific application and provides technical and commercial value.

TABLE III

The light pipe engine feature set.

| | |
|---|---|
| Wavelengths | UV-Vis-NIR |
| Colors | Up to eight |
| Intensity | 1-10 W/cm$^2$ |
| Bandwidths | Adjustable |
| Size | Compact |
| Ease of Use | Yes |
| Modulation | Up to 5 kHz |
| Color control | Independent |
| System Control | Manual or computer |
| Heat output | Minimal |
| Life time | Long |

Spectral Bands and Output Power

Figure 2:
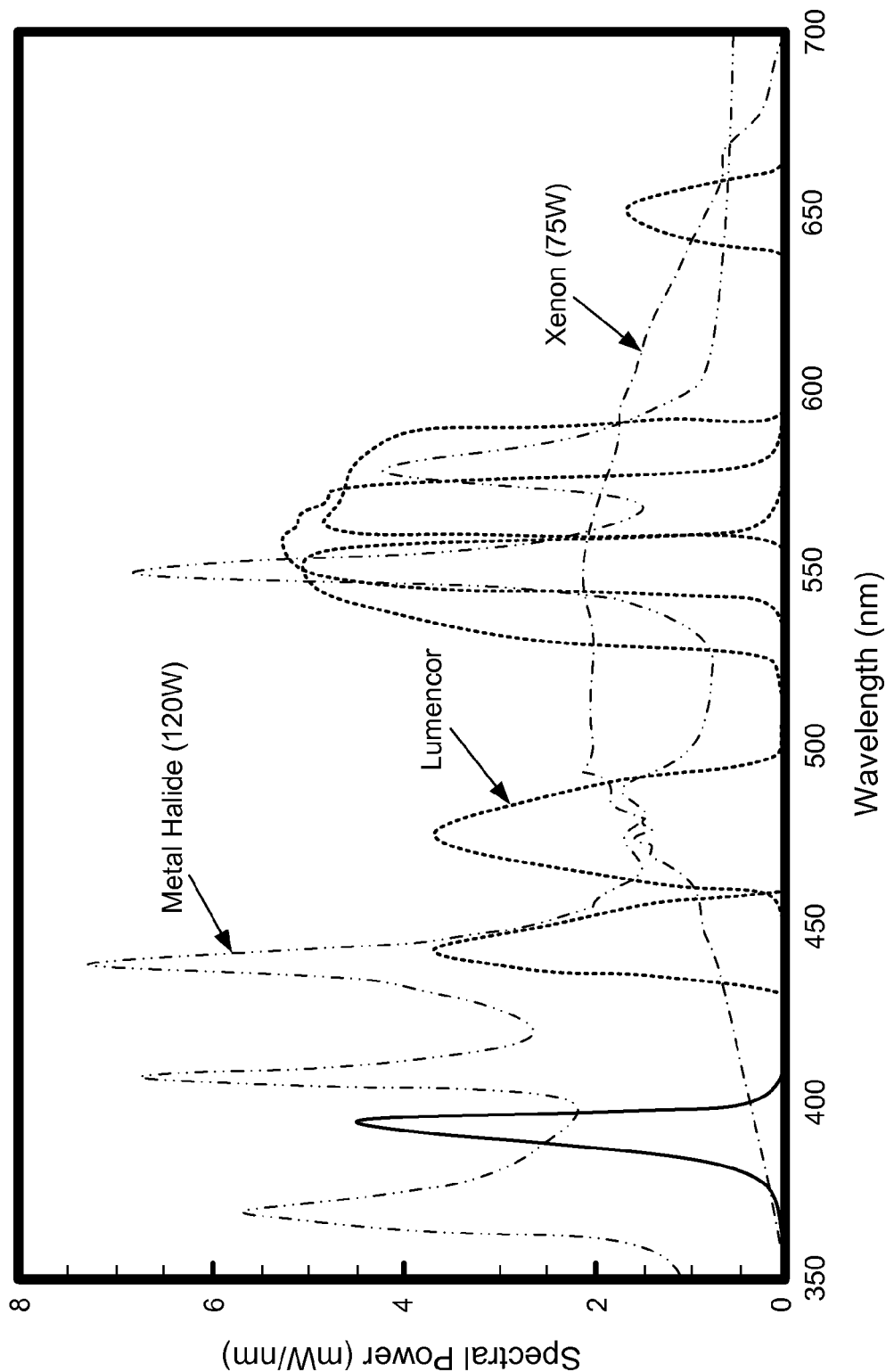
FIG. 2 shows light engine output relative to a typical metal halide lamp and 75 W xenon bulb.

In various embodiments of the present invention, the light pipe engine performs well compared with the output power across the visible spectrum to other lamps (see FIG. 2). Such comparisons beg for disclaimers as the outputs of the commonly employed lamps change in time and degrade with usage. The light pipe engine is all solid state so they it is significantly more stable and reproducible. FIG. 2 was taken within the manufacturers' specified lifetime for each lamp, by an independent user well trained in biophotonics, these outputs represent typical performances of a common metal halide bulb, 75 W xenon bulb and that of the light pipe engine.

Such output comparisons are further complicated by mismatches between the spikes of the metal halide bulb and light pipe light engine output bands, However, noting such disparities it is fair to claim the outputs of the light engine across the visible spectrum compare well against the outputs of a metal halide bulb in spectral windows that match the excitation energies of some of the most commonly used fluors for biotech: around 390 nm where DAPI and Hoescht can be excited; in the window most commonly associated with a cyan line of an argon ion laser and often used to excite Alexa dyes, green fluorescent proteins and fluoresceins; and in the red where neither of the lamps provides appreciable power for the likes of Cy5. The light engine also bests the Xenon lamp across the palate of excitation wavelengths most common to biotech: the Xenon lamp underperforms particularly in the violet, cyan, blue and red regions of the visible spectrum. Of course, more powerful Xenon lamps are often employed to provide enhanced performance at a significant maintenance cost.

In another embodiment of the present invention, as seen in FIG. 2, the output of the green and amber bands have essentially doubled, such that on a photon per photon basis the area under the curve for the arc lamp vs. light engine are the same. Certainly the peak shapes, and figures of merit (height, FWHM, etc.) differ. However, no compromise in output power, even for the 546 nm band of the arc lamp, should be incurred as a consequence of using a light pipe engine replacement.

Alternatively, a light pipe engine can be employed in a short duty cycle mode for power starved applications. When feasible, pulse widths of less than 100 ms at 10% duty cycles can actually improve the power output per band by a factor of 1.5 to 2.0 over longer duty cycles or in continuous mode of operation. Applications that employ multiple lasers and acousto-optic tunable filters (AOTFs) but need safe, cost effective and easy to employ lighting solutions might benefit from such light engine performance. Fluorescence microscopy for multicolor detection could take advantage of this option, for example. As could numerous other bioanalytical platforms such as a light engine replacement for the optical excitation from AOTF-based multicolor fluorescence detection for short tandem repeat (STR) analysis in a micro-eletrophoretic device, a glass microchip.

Fast Switching

Figure 3:
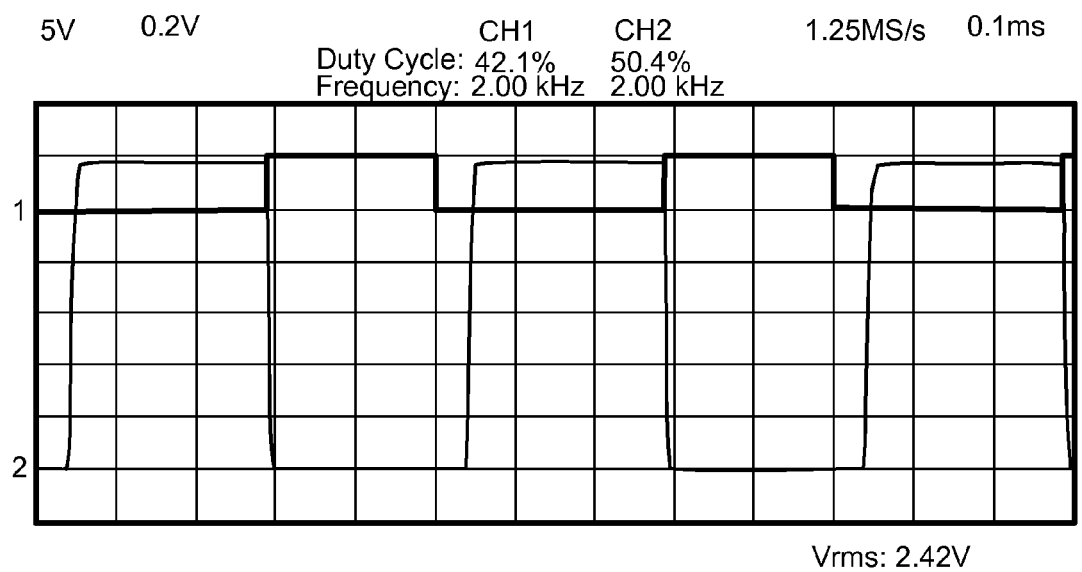
FIG. 3 shows light pipe engine with <10 ns rise and fall times for fast switching between bands.

Because of the solid state nature and independently operable designs of the lamp modules, coupled to fast (approximately 10 ns) decay times of typical materials employed, a light pipe based light engine outperforms any broad spectrum source in terms of support for fast analyses. Lamp based sources are coupled to filters and/or shutters with mechanical supports that relegate them 1 to 50 millisecond regimes. Even LED based lamps require filtering for most quantitative fluorescence based analyses. The light pipe based light engine incorporates all that filtering into its highly integrated design. Therefore switching times are limited today by the electronics of the boards controlling the sources. Rise times of less than 20 μs and fall times of less than 2 us are typical (see FIG. 3). Moreover each color can be switched independently and is compatible with triggering by TTL, RS232 and USB and intensity control by RS232, USB or manually. This supports experiments where simultaneous excitation of multiple tags could previously only be done with multipass excitation filters and broadband sources. Using a light pipe engine, effectively instantaneous excitation of individual reporters can be manipulated within microsecond time frames to achieve rapid, serial exposure of a biologic event to the various excitation bands with no external hardware beyond the light engine itself.

Stability

Figure 4:
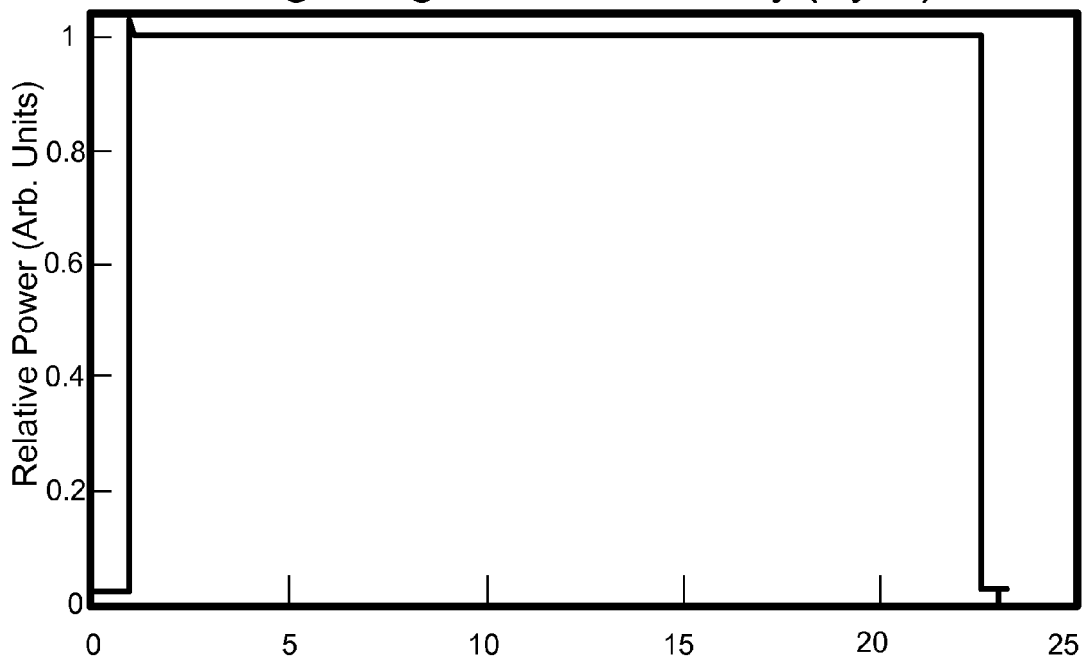
FIG. 4 shows light engine stability over 24 hours of use.

Because a light pipe based light engine is based on solid state technologies, they are extremely stable both in short duration experiments and over long term use. FIG. 4 depicts this stability. Light engines are powered by 24 V power supplies operated in DC mode, therefore there is no 60 Hz noise. All colors perform similarly. In 24 hours of continuous operation, the output fluctuates on the order of 1%. Short term stability on the order of 1.0 ms is approximately 0.5%. Short term stability for 0.1 ms is diminished by a factor of ten to 0.05%.

Eight Color Light Engine Subsystem

Figure 5:
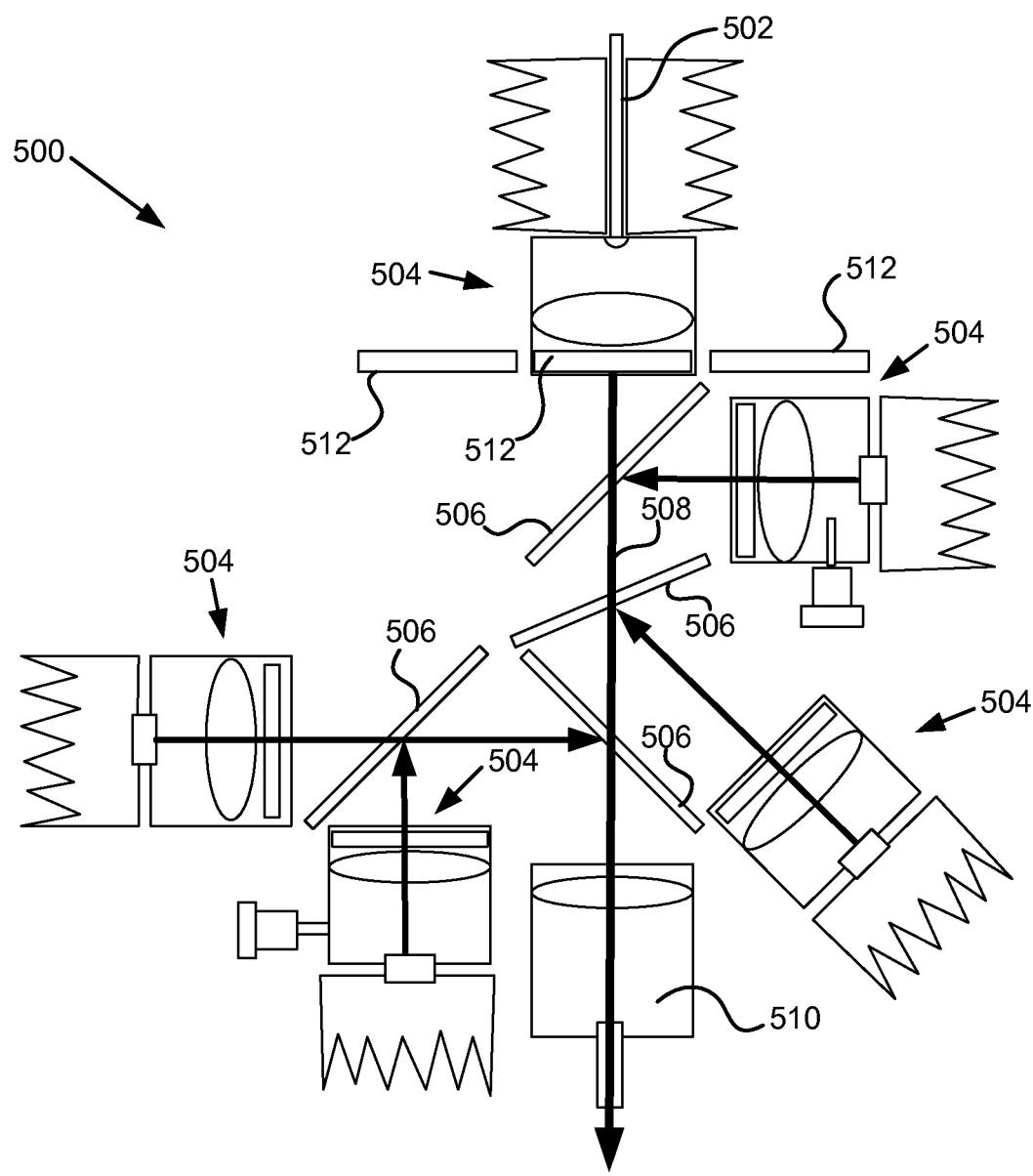
FIG. 5 shows a eight color light engine layout, including a light pipe and five other solid state light sources, with dichroic mirrors to create a single coaxial 8-color beam.

FIG. 5 shows a schematic for an eight color light engine layout. In an embodiment of the invention, a eight color light engine 500 includes a luminescent rod 502 and five other solid state light sources 504, with dichroic mirrors 506 to create a single coaxial 8-color beam 508 (for example selected from UV 395, Blue 440, Cyan 485, Teal 515, Green 550 or 575, Orange 630 and Red 650 nm) leading to an output 510. Each individual light source is collimated so as to be efficiently combined and after color combination, the beam is refocused into a light guide for transport to the device or system to be illuminated according to an embodiment of the invention. In this embodiment, a manual or electromechanical filter slider 512 allows green yellow filtering of YAG generating 550 or 575 nm light. Additional colors can be used. For example, a color band centered at 550 nm can be replaced with a color band centered at 560 nm. Each individual light source is collimated so as to be efficiently combined and after color combination, the beam is refocused into a light guide for transport to the device or system to be illuminated according to an embodiment of the invention.

The light engine subsystem is designed to interface to the array of bioanalytical tools with the expectation that the end user can take for granted the high quality of the illumination. Table IV summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ring-lights at the objective and fiber optic lights pointed at the specimen from the side. In both cases, the light engine must efficiently couple to a fiber optic cable.

arc light, Metal Halide and Xenon white-light sources for applications in microscopy, fluorescence microscopy. The solid state illumination system utilizes multiple solid state light sources operating simultaneously to generate one white light output. The solid state illumination system 600 generates white light which is continuous in the visible spectrum from 380 nm to 650 nm, has a high color rendering index, including ultraviolet, and is suitable for imaging all the most common fluorophores and fluorescent proteins. The white light can be modulated using external bandpass filters.

In a preferred embodiment the total output power is approximately 2.5 W. Advantageously, the spectral power of the solid state illumination system 600 is equal to or greater than the spectral power of a 120 W metal halide lamp or 150 W Xenon lamp across substantially the entire visible spectrum from 380 nm to 650 nm. This solid state light source of the present invention is substantially different that prior art devices for microscopy that provide light of a selected color

TABLE IV

Performance and cost analysis of the light pipe engine vs. traditional illumination subsystems in four key bioanalytical applications

| specification Light engine | Sanger Sequencing | | Q-PCR | | Flow Cytometry | | Fluorescence Microscopy | |
|---|---|---|---|---|---|---|---|---|
| | Light Pipe | Ar Ion Laser | Light Pipe | Metal Halide | Light Pipe | Lasers | Light Pipe | Metal Halide |
| Intensity W/cm$^2$ | 150-250 | 150-250 | 0.5-1 | 0.2-1, very λ specific | 150-250 | 150-250 | <50 | 1-50, very λ specific |
| Wavelength | 505 nm | multiline | 4 colors | | >2 colors | | 4 colors | |
| Bandwidth, nm | 10-30 | 26 | 10-30 | 15 | 10-30 | <5 | 10-30 | 15 |
| Stability | 0.1% | >1% | 0.1% | >1% | 0.1% | >1% | 0.1% | >1% |
| Switching, ms | <0.03 | 1-10, ext. shutter | <0.03 | 40, ext. shutter | <0.03 | 1-10, ext. shutter | <0.03 | 40, ext. shutter |
| MTBF, hrs | >10,000 | <4,000 | >10,000 | <1,000 | >10,000 | <4,000 | >10,000 | <1,500 |
| Price | <$3K | >$5K | <$7.5K | >$10K | <$5K | >$5K | <$7.5K | >$10K |

For portable diagnostic tools, the delivery optics must provide even illumination over a small volume. These requirements are similar to, but less restrictive than those presented by capillary electrophoresis. Capillary electrophoresis requires an intense (10 mW) light focused onto the side of a capillary tube with characteristic dimensions on the order of a 350 pm outer diameter and a 50 pro inner diameter. To achieve this goal, the delivery optics were comprised of a ball lens to collect and collimate light from the lamp module (already coupled into an optical fiber), a bandpass filter to provide a narrow bandwidth of illumination, and an aspheric lens to focus the light at the center of the capillary bore. This approach yielded an 80 pin spot size and the desired 10 mW of delivered power to the capillary tube.

The design of delivery optics for microfluidic immunoassays requires both the even illumination required for optical microscopy and the small volume illumination required for capillary electrophoresis. Light engines capable of delivering even illumination at the active sites in a microfluidic array for detection of fluorescent tagged biomarkers have been designed for immunochemical as well as genomic applications. The advantages of the luminescent light pipe are providing commercial, readily available light engine solutions for illumination-detection platforms optimized for portable diagnostic tools.

Solid State Source of Continuous White Light

Figure 6B:
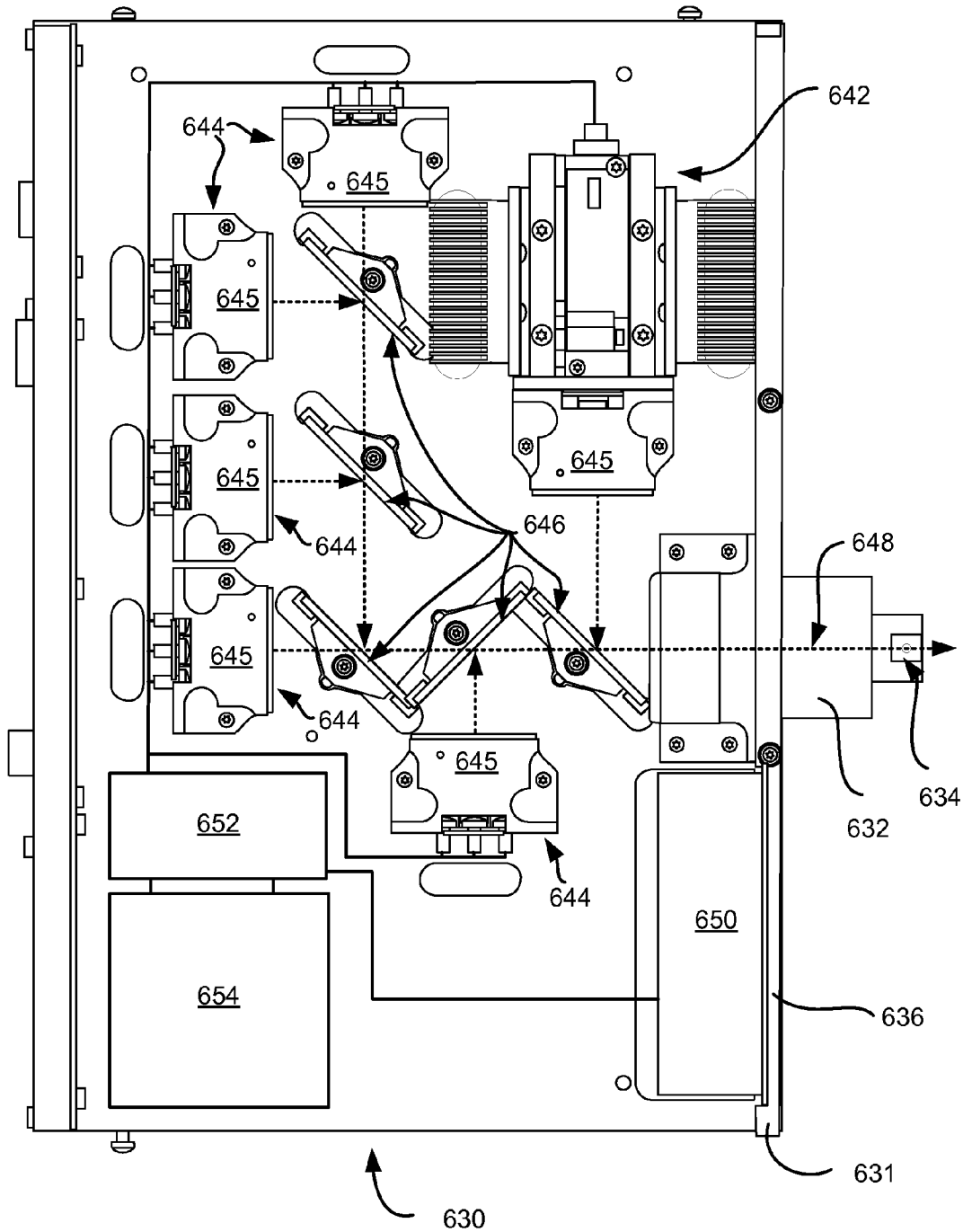
FIG. 6B shows a plan view of the components of the solid state white light subsystem of the white light illumination system of FIG. 6A.
Figure 6C:
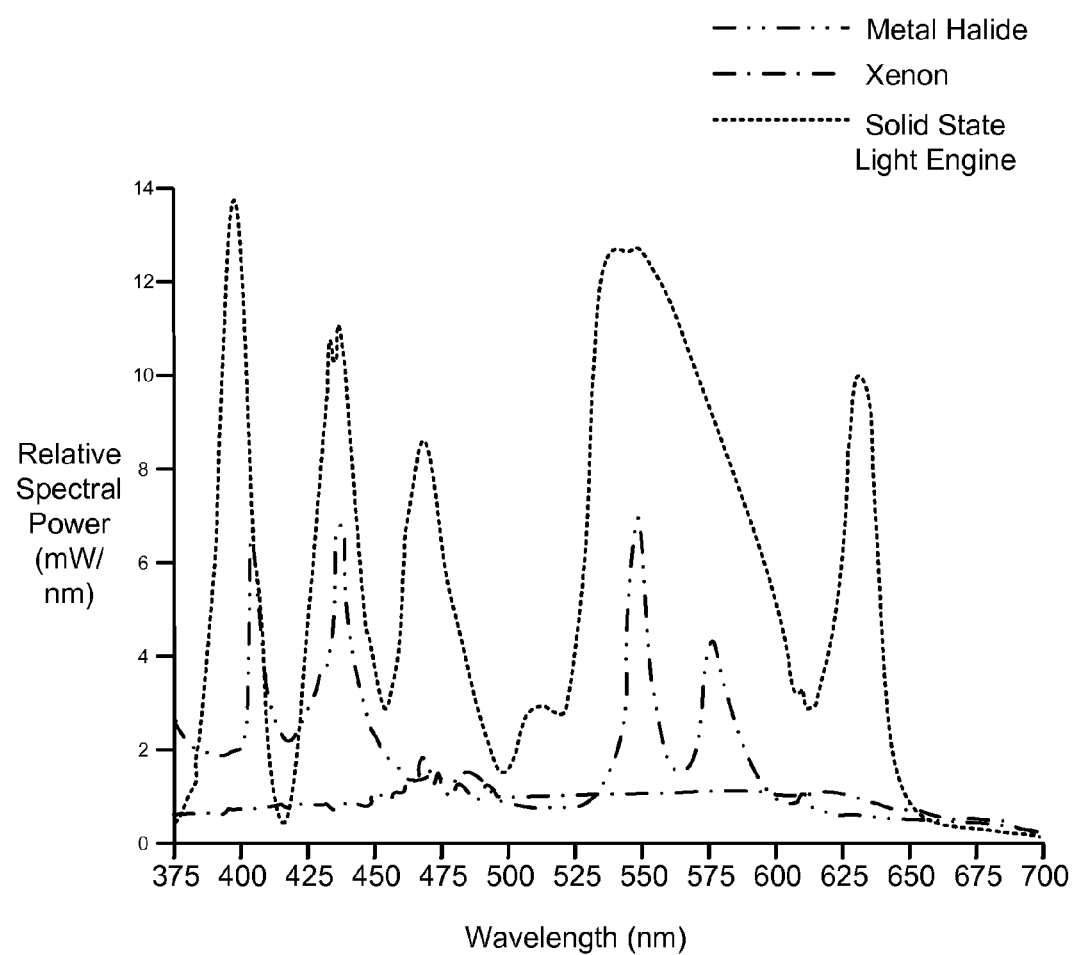
FIG. 6C is a graph showing spectral power of the solid state white light subsystem of FIG. 6B in comparison to a 120 W metal halide lamp and a 175 W Xenon lamp.

FIGS. 6A-6C shows aspects of a solid state illumination system 600 suitable for use as a replacement for conventional for microscopy rather than providing continuous spectrum white light which can be externally filtered downstream—for example using filter systems previous only suitable for arc lamps—thus the user can utilize a broad range of commercially available filters. This provides the most flexibility to the user in utilizing the light output.

FIG. 6A shows the solid illumination system 600; FIG. 6B shows a plan view of the components of the solid state light engine 630 of the solid state illumination system of FIG. 6A; and FIG. 6C is a graph showing spectral power of the solid state light engine of FIG. 6B in comparison to a 120 W metal halide lamp and a 175 W Xenon lamp. Referring first to FIG. 6A which shows solid state illumination system 600. As shown in FIG. 6A, solid state illumination system 600 includes a flexible fiber optic 610, a filter system 620, and a solid state light engine 630. Solid state light engine 630, includes a liquid light guide 632 mounted on the exterior of housing 631 of solid state light engine 630. Liquid light guide 632 includes an aperture 634 through which white light is provided from solid state light engine 630. Liquid light guide 632 includes a coupling for connecting external filter system 620 and/or flexible fiber optic 610 to solid state light engine 630 such that white light from aperture 634 is efficiently coupled to external filter system 620 and/or flexible fiber optic 610. A grill 636 allows flow of air through housing 631 for cooling the light sources.

Filter system 620 includes one or more light filters 622 which can be placed in the path of the white light exiting from aperture 634. As shown in FIG. 6A, filter system 620 includes a slot 624 designed to receives a filter paddle 623 holding a light filter 622. A range of filter paddle/filter combinations is provided in order that a user can modify the white light according to the users needs. Alternatively, an automated and/or computer controlled filter system can be utilized. For example a motorized filter wheel including a plurality of different filters can be used—a controller allows the selection and positioning of the desired filter in the light path. Alternatively, in some embodiments filter system 620 can comprise a filter cube including a dichroic mirror mounted on an optical block for use in florescence microscopy. Such filter cubes are typically mounted directly to the microscope rather than the solid state light engine 630. Advantageously, by providing continuous white light as an output the solid state light engine 630 allows for the use of conventional filter systems utilized with arc lamps.

Flexible fiber optic 610 is used to connect solid state light engine 630 to an optical system such as a microscope or endoscope. Adapters are provided to connect flexible fiber optic 610 to a range of microscope, endoscope and/or other desired optical systems requiring illumination. Flexible fiber optic 610 transmits light from solid state light engine 630 along its length to the optical system through optical fibers and or a liquid medium. Flexible fiber optic 610 is in some case connected between solid state light engine 630 and filter system 620 (for example where filter system 620 is mounted directly to a microscope. In other cases, flexible fiber optic 610 is connected to a coupling of filter system 620 as shown in FIG. 6A.

The light engine subsystem is designed to interface to the array of bioanalytical tools with the expectation that the end user can take for granted the high quality of the illumination. Table IV (above) summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ringlights at the objective and fiber optic lights pointed at the specimen from the side. In both cases, the light engine must efficiently couple to a fiber optic cable and thence to the particular bioanalytical tool.

FIG. 6B shows a plan view of the components of the solid state light engine 630 of the solid state illumination system. As shown in FIG. 6B, housing 631 contains a light pipe engine 642, and five LED light sources 644, and a plurality of dichroic mirrors 646. Each individual light source is collimated so as to be efficiently combined and after color combination, the beam is refocused into a light guide for transport to the device or system to be illuminated. The light pipe engine 642 and the LED light sources 644 each include output optics 645 to image and collimate the light output of the source into a beam that can be imaged on the input aperture of the liquid light guide 632. The light pipe engine 642, the LED light sources 644, and dichroic mirrors 646 are arranged to create a single coaxial beam of light 648 which is directed at the input aperture of the liquid light guide 632 as shown by the dashed arrows. In a preferred embodiment, the light beam 648 output is white light which is substantially continuous over the visible spectrum of 380 nm-680 nm and includes no ultraviolet or infrared light.

Housing 631 also contains a fan 650, controller 652, and power supply 654. Housing 631 can also contain one or more sensors (not shown) to analyze the spectral content of beam 648. Power supply can be an AC/DC transformer for wired applications or may alternatively be a battery for portable applications.

LED light sources 644 and light pipe engine 642 are selected to provide different color components of the spectral content of the continuous white light output. In a preferred embodiment there are five LED light sources 644 each producing a different color component of the continuous white light output. The output wavelengths of the sources overlap and combine to some extent contributing the overall spectral output of the solid state light engine 630. The LED light sources are ganged together and with the light pipe engine 642. In embodiments the LED light sources 644 and light pipe engine 642 produce spectral components centered on colors violet 395 nm, blue 425-460 nm, cyan 460-500 nm, teal 515 nm, green 500-615 nm, and red/orange 615-685 nm. All of LED light sources 644 and light pipe engine 642 are turned on at the same time such that the different colors are combined to create a substantially continuous white light having a high color rendering index (CRI). In alternative embodiments, a second light pipe engine 642 can be used in place of one or more of the direct LED light sources 644.

In a preferred embodiment light pipe engine 642 is used to generate green (green and yellow) light spanning 500-600 nm. LED lights that emit green light at high power are notoriously difficult to create—the so-called green gap. Thus light pipe engine 642 utilizes high power blue LED light sources to excite a luminescent rod which emits green light spanning 500-600 nm. In a preferred embodiment light pipe engine utilizes two arrays of 40 blue LEDs to excite emission of green light from the luminescent rod. A suitable light pipe engine 100 is described above with respect to FIG. 1. Suitable light engines are also described in the Related Applications listed above and incorporated herein by reference. The luminescent rod of the light pipe engine can be convectively cooled as previously described or conductively cooled by being clamped into contact with a metal pedestal heat sink (for example a copper heat sink.) A light pipe engine operating to generate green light allows the solid state light engine 630 to produce an output in the green and amber bands that is the same or greater than commonly used arc lamps (see, e.g. FIG. 6C). Thus, no compromise in output power, even for the 546 nm band of the arc lamp, is be incurred as a consequence of using solid state light engine 630 as a replacement for an arc lamp.

As shown in FIG. 6B controller 652 is connected to each of the LED light sources 644 and light pipe engine 642. In a preferred embodiment, control of all of LED light sources 644 and light pipe engine 642 is ganged. For example, each of the LED light sources 644 and light pipe engine 642 is turned on and off at the same time and the power of each of the LED light sources 644 and light pipe engine 642 is modulated in the same way. Thus if one LED light source is dimmed by 50% all of the LED light sources 644 and light pipe engine are dimmed by 50%. To put it another way, as the light output of the preferred embodiment is desired to be white light, the LED light sources 644 and light pipe engine cannot be independently turned off an on or independently adjusted in power output. To the extent that a user desires to alter the spectral content of the white light, the user is required to modulate the white light with filters placed in the white light beam 648. Typically this is done using external bandpass filters in filter system 620.

Controller 652 communicates with software, cameras, microscopes, remote controls, and/or foot pedals to allow control of solid state light engine 630. For example in a preferred embodiment UNIBLITZ® command control is supported for on/off synchronization in place of an electronic shutter. For additional example, a remote control accessory can be used to facilitate control by allowing user operation without a dedicated computer or third party software. A remote control accessory can be compatible with 3rd party software control of the illuminator but simplifies light engine operation and reduces start up time. A camera interface provides exact synchronization in a complete imaging system. The camera interface to controller 652 eliminates lag time, minimizes photo-damage to sensitive samples, and ensures exposure of biological samples to only the required amount of light needed for a given experiment.

Because solid state light sources are used, the light engine can be turned on and off at a high switching speed not possible with arc lamps. For example, in an embodiment, the switching speed can be up to 5 kHz with turn on/off in approximately 10 µs. The high switching speed enable light blanking during frame readout thereby minimizing photobleaching during sample illumination and prolonging sample life. The short warm-up time of the system and superior stability of the solid state light sources provide for highly reproducible output power as well as a long expected lifetime greater than 15,000 hours without the need for arc lamp alignment, installation and replacement. Moreover, the solid state light engine also produces less heat, thus reducing the power and cooling requirements of the system as compared to arc lamp systems.

FIG. 6C is a graph showing spectral power of the solid state light engine of FIG. 6B in comparison to commonly used 120 W metal halide lamps and a 175 W Xenon lamps. As shown in FIG. 6C, the solid state light engine 630 generates white light which is continuous in the visible spectrum from 380 nm to 650 nm and is suitable for imaging all the most common fluorophores and fluorescent proteins. Advantageously, the spectral power of the solid state illumination system 600 is equal to or greater than the spectral power of a 120 W metal halide lamp or 150 W Xenon lamp across substantially the entire visible spectrum from 380 nm to 650 nm. In particular embodiments the spectral power is greater than 1 mW/nm over the substantially the entire visible spectrum from 380 nm to 650 nm and greater than 3 mW/nm over the range from 500-600 nm. The continuous white light provided solid state light engine 630 provides white light having a high color rendering index. Moreover, the color temperature, and other attributes of the white light can readily be modulated with external filters in filter system 120. Thus solid state light engine 630 can serve as a direct replacement for 120 W metal halide lamp or 150 W Xenon lamps.

In alternative embodiments, controller 652 can be designed to control LED light sources 644 and light pipe engine 642 individually (on/off and intensity) such that the spectral content of the output light can be modulated and/or changed in color. Moreover, in an alternative embodiment, filter system 620 can be integrated into housing 631 such that filters 622 can be inserted into the output light path manually (for example through a slot in the housing) or under the control of controller 652 (for example a motorized-controlled filter wheel).

Hybrid Optical and Electrical Intensity Control

In certain embodiments of the invention, it is desirable to control the intensity of the light output by the light engine. Embodiments of the invention utilize hybrid optical and electrical intensity control such that the output intensity can be linearly controlled without substantially altering the relative spectral power distribution of the light. The hybrid electrical and optical attenuation system allows for varying the intensity of the selected spectral power distribution without substantially altering the selected spectral power distribution over a greater range of intensities than would be possible with purely electrical control. The system is suitable for use with white light engines or light engines designed to produce selectable colors/wavelengths of light.

The intensity of the light generated by the LED light sources 644 and LED light pipe engine 642 can be electronically controlled by controller 652. Controller 652 provides a pulsed electrical signal to the LEDs of the LED light sources 644 and LED light pipe engine 642 at a current and voltage suitable for causing the LEDs to emit light. In a preferred embodiment the controller 652 can vary the current supplied to the LEDs in order to control the intensity of light emitted by the LEDs and consequently the LED light sources 644 and LED light pipe engine 642 of which they are part. When electronically controlling the intensity of the light generated by the LED light sources 640 and LED light pipe engine using controller 652, the intensity of the light generated can be controlled without altering the spectral power distribution of the LEDs over a substantial range of intensity. However, when operated at low power, the spectral power distribution of the light emitted by the LEDs can change for a number of reasons.

The electrical and optical characteristics of an LED are temperature dependent. Thus the light generated by an LED can vary based upon the temperature of the LED. The temperature of the LED is affected by the heat generated by the LED and the heat flux out of the LED. When operated at lower currents (lower power), the amount of heat generated within the LED is reduced which can cause the temperature of the LED to drop. Thus, the temperature of the LED can vary based upon the power at which the LED is driven thereby changing the electrical and optical characteristics of the LED.

In particular, the spectral output of an LED can be affected by the operating temperature of the junction in the LED. Thus, varying the power (current) at which the LED is driven can alter the spectral power distribution of the light output by the LED. The effect of varying the power at which the LED is driven on the spectral power distribution of an LED depends upon the chemistry, design and manufacture of the LED. Different colored LEDs have different chemistries, and can also have different design and manufacture. For example different colored LEDs are manufactured using different III-V alloy compounds. Thus, the variation of spectral power distribution at low power operation is likely to be different for different colors of LEDs.

The variation of spectral power distribution dependent on intensity is compounded in a system in which the output of several different colored LEDs is combined into a single output beam. As intensity of the output beam is reduced by changing the power at which the LEDs are driven, the individual sources may each change in spectral power distribution. The point at which the spectral power distribution changes for each source can be different, so too the character of the change. Thus the spectral power distribution of the combined output beam can be significantly and/or unpredictably affected over a range of low power intensities. However, it is desirable to have a large dynamic range of output beam intensity without significant changes in spectral power distribution.

According to embodiments of the present invention, a system is provided for hybrid optical and electrical control of output intensity. In general terms, the light output of one or more of the LED light sources and/or and LED light pipe engine is attenuated optically such that it is not necessary to reduce the electrical power (drive current) provided to the LEDs within the source at a level where the spectral power distribution of the LEDs is variable. One way of achieving optical attenuation of the light output is through the use of a neutral density filter. Another way of achieving optical attenuation of the light output is repositioning of the optical elements within output collimating optics such that a smaller fraction of the output of the LED components is imaged and collimated into the beam that is directed towards the optical pathway in which the outputs are combined and thereby directed to the output and any device connected thereto.

A neutral density filter is an optical component, typically a flat sheet or plate, which blocks a portion of light passing through it. Significantly, a neutral density filter is designed such that it affects all wavelengths of light equally (within its designated range). Transmission (T) of light through a neutral density filter is dependent upon density (D) such that the percentage of light transmitted $T=10^{-D}\times100$. Since the transmission value is substantially the same for all wavelengths of light within a specified range, there is no effect on spectral power distribution. That is the absolute power is reduced at all wavelengths in the light equally such that there is no substantial change in the relative power of different wavelength components of the light. Neutral density filters suitable for use in the present invention can have optical densities up to 2 and transmission of between 99% and 1% depending of the degree of optical attenuation required. Multiple neutral density filters can be used in combination to further attenuate the light (the optical density of multiple neutral density filters can be calculated by addition of the optical densities of each filter).

Absorptive neutral density filters attenuate light by absorption of the non-transmitted portion with minimal reflection. An absorptive neutral density filter can also be treated with a non-reflective coating to further reduce reflection of light back towards the LEDs. Reflective neutral density filters reflect the non-transmitted portion of the incident light back towards the source. Continuously variable neutral density filters have an optical density that varies linearly along the length of a plate or around the circumference of a circular filter. Moving two such filters differentially allows for selectively controlled transmission of an optical beam.

For example an LED light source may have a stable spectral power distribution when electrically driven at between 10% to 100% of its maximum output intensity but varies in spectral power distribution when electrically driven between 0 and 10% of its maximum output intensity. It is thus, problematic using solely the electronic controller to generate an output beam of 8% of maximum intensity because the spectral power distribution can vary. If however, the output is optically attenuated by 50%, such as by interposing a neutral density filter in the output path which transmits only half of the light (Transmission=50%, Optical Density=0.3), when electrically driven at 10% of its maximum output, the LED light source will output half as much light. Thus, the attenuated LED light source can now have a stable spectral power distribution when electrically driven anywhere between 5% and 100% of its maximum output intensity. For example, an output beam of 8% of maximum unattenuated intensity can now be achieved by electrically driving the LED source at 16% of its maximum electrical power/current which is within the range of power/current where the spectral power distribution is stable. Note however that, if the optical attenuation is fixed, the maximum output intensity be will also be reduced by half compared to the LED light source without optical attenuation.

The optical attenuation of the light output can be fixed or variable. Where the optical attenuation is variable it can be made continuously variable by, for example, using a continuously variable neutral density filter wheel operated by a motor/servo or manually. Alternatively, the optical attenuation can be made stepwise variable by, for example motor/servo or manually controlled insertion of a selected neutral density filter into the optical output beam of an individual source.

Thus, for example, in one embodiment of a variable optical attenuation system, a neutral density filter which transmits half of the light is provided which can be selectively interposed in the output beam of each individual source (or one or more of the sources). Thus, for example, the neutral density filter is removed from the output beam (either manually or under motor/servo control) when high power output is desired (between 10 and 100% of unattenuated maximum) and then interposed in the output beam (either manually or under motor/servo control) when low power output is desired (between 5 and 50% of unattenuated maximum). Likewise a 25% transmission neutral density filter can be interposed when low power output is desired (between 2.5% and 25% of unattenuated maximum). Likewise a 10% transmission neutral density filter can be interposed when low power output is desired (between 1% and 10% of unattenuated maximum).

In an alternative embodiment of a variable optical attenuation system a continuously variable neutral density filter is interposed in the output beam of one or more sources with the light engine. The continuously variable neutral density filter is capable of transmitting from almost 0% to 100% of the output beam depending upon the position of the filter. When high power output is desired (between 10 and 100% of non-attenuated maximum) the continuously variable neutral density filter is positioned such that it blocks 0% of the output beam. If output power below 10% of non-attenuated maximum is required, the LED is still electrically driven at 10% (or higher) of its maximum output and the continuously variable neutral density filter is moved such that it attenuates the output by transmitting a selectable amount (100% to almost 0%) of the output beam without altering the spectral power distribution. In such a manner the intensity of the output beam can be controlled from 100% to almost 0% of its non-attenuated maximum without affecting the spectral power distribution of the beam with power/current used to control intensity between 100% and 10% and optical attenuation used to control intensity below 10%.

Note that it would also be possible to achieve the above result using the continuously variable neutral density filter alone while electrically driving the LED at 100% of its maximum output. However, this is undesirable as the light blocked by neutral density filter is dissipated inside the light engine as heat. In the case of an absorptive neutral density filter, the filter itself absorbs and is heated by the light which is not transmitted—were the LED driven at 100% of its maximum output the heat generated in the neutral density filter might be damaging to the neutral density filter or other components of the light engine. Thus, it is preferable to use a combination of control using both electronic control and optical attenuation to achieve the desired range of optical intensity control while maintaining uniform spectral power distribution.

Figure 6D:
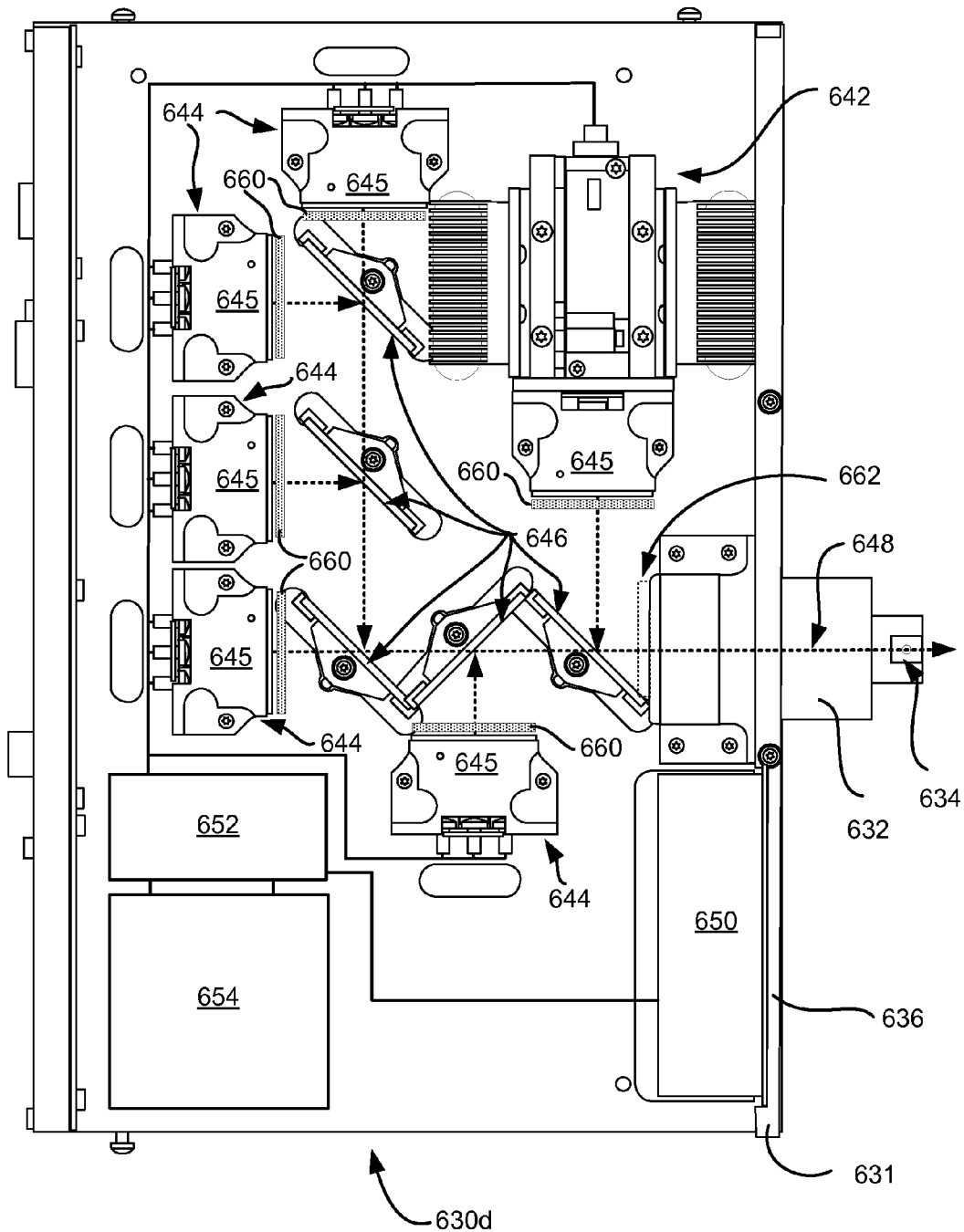
FIG. 6D shows a plan view of the components of a variation of the solid state white light subsystem of the white light illumination system of FIG. 6A.

FIG. 6D shows a plan view of the components of a variation 630d of the solid state light engine 630 of the solid state illumination system of FIG. 6A in which components are provided for hybrid optical and electrical control of output intensity. In general terms, the light output of one or more of the LED light sources 640 and LED light pipe engine 645 is attenuated optically such that it is not necessary to reduce the drive power of the LEDs within the source into the region where the spectral power distribution begins to change. As shown in FIG. 6D, one way of achieving optical attenuation of the light output is through the use of one or more neutral density filters interposed between one or more of the LED light sources 640 and LED light pipe engine 645 and dichroic mirrors 646 such that the collimated beam of light exiting the source must pass through the neutral density filter 660 before joining the optical pathway which combines the beams and directs them towards liquid light guide 632 and aperture 634.

Neutral density filters 660 are selected such that they affects all wavelengths of light equally within the range of wavelengths output be the light sources 640 or LED light pipe engine 645 with which they are used. Thus different types of neutral density filter can be used for example for different wavelengths of light to ensure that the spectral power distribution is not affected by the particular neutral density filter used.

Note that it is possible, in an alternative embodiment to position a fixed, variable or selectable neutral density filter in the combined output beam—for example at position 662 of FIG. 6D. While a neutral density filter at this position would attenuated the output from all the sources it would not allow for the use of different neutral density filters of different types and densities suitable for the individual sources. Moreover, while neutral density filters are designed to attenuate all wavelengths of light equally within their specified range, they are not perfect. Thus, it is preferable to use different neutral density filters selected for each source to attenuate the particular wavelengths of each source without substantially changing the spectral power distribution of that source rather than attenuated all of the combined wavelengths with a single neutral density filter in the combined beam.

The optical density of each neutral density filter may be identical. Alternatively one or more the neutral density filters 660 may have a different the optical density to account for the particular characteristics of the light source and the requirement to modulate the intensity of the light provided by that source. Moreover, although neutral density filters 660 are shown adjacent each light source in the embodiment of FIG. 6D, one or more of the LED light sources 640 and LED light pipe engine 645 may not be provided with a neutral density filter if the source has adequate uniformity of spectral power distribution over the desired range of intensities. It should be noted, that where the optical attenuation of the LED light sources is different, the controller should be adjusted to electrically drive the sources to achieve the appropriate spectral power distribution in the output beam. Thus, for example if a selected source is optically attenuated with a neutral density filter having 50% transmission and the other sources are not optically attenuated, the controller should drive the selected source with double the electrical power in order to achieve the same spectral power distribution in the output beam as achieved by the system without optical attenuation.

Neutral density filters 660 are in some embodiments fixed in place during manufacture of the solid state light engine 630d of the solid state illumination system of FIG. 6A. If the neutral density filters 660 have a fixed optical density, the optical density is selected such that the combined output light has an intensity which can be varied over the desired range of an end user of the device without substantially changing the combined spectral power distribution of the combined output light. Thus neutral density filters 660 can have different optical densities in different units depending on the end user's desired application and desired spectral power distribution and range of intensity control.

Neutral density filters 660 are in some embodiments selectable. For example, a filter slot can be provided such that the user can selectable interpose or remove the neutral density filters from the positions shown. Alternative a motor or servo controlled mechanism can selectable interpose or remove the neutral density filter from the output beam of a particular LED source under control of controller 652. Thus, the user or controller can select to interpose neutral density filters in front of the sources in order to operate in a low intensity mode or remove the filters to achieve maximum intensity of power output. As previously indicated, unless the optical attenuation of all the LED light sources is substantially the same, the controller 652 should be configured to adjust the relative electrical power to the LED light sources to compensate for the differences in optical attenuation and thereby ensure that the spectral power distribution is substantially the same with and without optical attenuation.

Neutral density filters 660 are, in some embodiments, variable. For example a continuously variable or stepped neutral density filter can be used. A manual device such as a dial can be used to control the selected transmission of the neutral density filters. If a manual device is used, the device should be selected to ensure that the output of each source is attenuated by the same amount so as not to alter the spectral power distribution of the combined light output. Alternatively, the position (and consequently transmission) of the continuously variable or stepped neutral density filter can be monitored and/or controlled by controller 652 such that the optical attenuation of each light source can be controlled by controller 652 and the controller can compensate for any different optical attenuation of each light source by adjusting the electrical power provided to the LEDs of the light sources.

Note that solid state light engine 630d of the solid state illumination system of FIG. 6A is designed to produce continuous white light output for which all of the LED light sources are varied in intensity in the same way to maintain a desired spectral power distribution within the white light. However, the hybrid electrical and optical attenuation system disclosed herein can also be used in solid state illumination systems designed to produce a selectable spectral power distribution such as by turning on one or more selected LED sources and turning off one or more unselected light sources. The hybrid electrical and optical attenuation system allows for varying the intensity of the selected spectral power distribution without substantially altering the selected spectral power distribution over a greater range of intensities than would be possible with purely electrical control.

The foregoing description of the various embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

The illumination systems and components thereof including the hybrid electrical and optical intensity control system described herein may, with suitable adaptation, find application in a range of applications including: life science applications which cover a range of white light and/or fluorescence analyses and quantitation; microscopy; fluorescence microscopy; high content screening; genetic expression analysis; digital pathology; and endoscopy.

Other features, aspects and objects of the invention can be obtained from a review of the figures and the claims. It is to be understood that other embodiments of the invention can be developed and fall within the spirit and scope of the invention and claims.

What is claimed is:

1. An illumination system, comprising:
   a plurality of LED light sources, wherein each of the plurality of LED light sources emits output light of a different color than each other of the plurality of LED light sources;
   an LED control circuit which controls the electrical power provided to the plurality of LED light sources such that intensity of light emitted by each of the plurality of LED light sources can be varied over a range;
   associated optics, wherein the associated optics combine the output light of different colors emitted by the first plurality of LED light sources into a combined output light having a combined spectral power distribution;
   a first optical attenuator interposed between a first LED light source of the plurality of light sources and the associated optics such that output light of said first LED light source is attenuated prior to combination by the associated optics; and
   a second optical attenuator interposed between a second LED light source of the plurality of light sources and the associated optics such that output light of said second LED light source is attenuated prior to combination by the associated optics;
   whereby the combined output light has an intensity which can be varied over a desired range without substantially varying the combined spectral power distribution of the combined output light.

2. The illumination system of claim 1, wherein said first optical attenuator and said second optical attenuator are neutral density filters.

3. The illumination system of claim 1, wherein said first optical attenuator and said second optical attenuator are a fixed neutral density filters having a transmission between 1% and 99%.

4. The illumination system of claim 1, wherein said first optical attenuator and said second optical attenuator are fixed neutral density filters having a transmission between 10% and 50%.

5. The illumination system of claim 1, wherein said first optical attenuator is a variable optical attenuator which has a selectable transmission between 100% and 1%.

6. The illumination system of claim 1, wherein:
   said first LED light source comprises one or more LEDs; and
   said first optical attenuator comprises collimating optics for collimating light emitted from the one or more LEDs to form said output light in combination with a mechanism for moving one or more elements of the collimating optics such that less of the light emitted from the one or more LEDs is collimated to form said output light.

7. The illumination system of claim 1, wherein the first plurality of LED light sources are ganged such that all of the plurality of LED light sources are turned on and off and varied in intensity together.

8. The illumination system of claim 1, wherein the plurality of LED light sources are ganged such that the plurality of LED light sources cannot be independently controlled.

9. The illumination system of claim 1, wherein the combined output light has an intensity which can be varied over a range from 2% to 100% without substantially changing the combined spectral power distribution of the combined output light.

10. The illumination system of claim 1, further comprising a filter system and a liquid light guide for providing the combined output light to a microscope system.

11. The illumination system of claim 1, wherein the combined output light is white light.

12. The illumination system of claim 1, wherein the combined output light has a selectable color.

13. The illumination system of claim 1, wherein the first optical attenuator and the second optical attenuator have substantially similar transmission properties.

14. The illumination system of claim 1, wherein the first optical attenuator has different transmission properties than the second optical attenuator.

15. An illumination system, comprising:
   a plurality of three or more LED light sources, wherein each of the plurality of LED light sources emits output light of a different color than each other of the first plurality of LED light sources;
   an LED control circuit which controls the electrical power provided to the first plurality of LED light sources such that intensity of light emitted by each of the plurality of LED light sources can be varied over a range;
   associated optics, wherein the associated optics combine the output light of different colors emitted by the first plurality of LED light sources into a combined output light having a combined spectral power distribution;
   a first optical attenuator interposed between a first LED light source of the plurality of light sources and the associated optics such that output light of said first LED light source is attenuated prior to combination by the associated optics; and
   a second optical attenuator interposed between a second LED light source of the plurality of light sources and the associated optics such that output light of said second LED light source is attenuated prior to combination by the associated optics;
   a third optical attenuator interposed between a third LED light source of the plurality of light sources and the associated optics such that output light of said third LED light source is attenuated prior to combination by the associated optics;
   whereby the combined output light has an intensity which can be varied over a desired range without substantially changed the combined spectral power distribution of the combined output light.

16. The illumination system of claim 15, wherein said first optical attenuator, said second optical attenuator, and said third optical attenuator are neutral density filters.

17. The illumination system of claim 15, wherein each of said first optical attenuator, said second optical attenuator, and said third optical attenuator is a fixed neutral density filter having a transmission between 1% and 99%.

18. The illumination system of claim 15, wherein each of said first optical attenuator, said second optical attenuator, and said third optical attenuator is a fixed neutral density filter having a transmission between 10% and 50%.

19. The illumination system of claim 15, wherein each of said first optical attenuator, said second optical attenuator, and said third optical attenuator is a variable optical attenuator which has a selectable transmission between 100% and 1%.

20. The illumination system of claim 15, wherein:
   said first LED light source comprises one or more LEDs; and
   said first optical attenuator comprises collimating optics for collimating light emitted from the one or more LEDs to form said output light in combination with a mechanism for moving one or more elements of the collimating optics such that less of the light emitted from the one or more LEDs is collimated to form said output light.

21. The illumination system of claim 15, wherein the combined output light has an intensity which can be varied over a range from 2% to 100% without substantially changing the combined spectral power distribution of the combined output light.

22. The illumination system of claim 15, wherein the combined output light is white light.

23. The illumination system of claim 15, wherein the combined output light has a selectable color.

24. The illumination system of claim 15, wherein a transmission of said first optical attenuator and said second optical attenuator and said third optical attenuator is substantially equivalent.

25. The illumination system of claim 15, comprising wherein a transmission of said first optical attenuator is different than at second optical attenuator.

* * * * *